US006046378A

United States Patent [19]

Quincy, III et al.

[11] Patent Number: 6,046,378

[45] Date of Patent: *Apr. 4, 2000

[54] WETTABLE ARTICLE

[75] Inventors: Roger Bradshaw Quincy, III, Alpharetta; Elizabeth Deibler Gadsby, Marietta, both of Ga.

[73] Assignee: Kimberly-Clark Worldwide, Inc., Neenah, Wis.

[*] Notice: This patent issued on a continued prosecution application filed under 37 CFR 1.53(d), and is subject to the twenty year patent term provisions of 35 U.S.C. 154(a)(2).

[21] Appl. No.: 08/820,403

[22] Filed: Mar. 12, 1997

Related U.S. Application Data

[63] Continuation of application No. 08/404,004, Mar. 14, 1995, abandoned.

[51] Int. Cl.$^7$ .............................. A61F 13/15; A61F 13/20
[52] U.S. Cl. .......................................................... 604/375
[58] Field of Search ...................................... 604/367–375

[56] References Cited

U.S. PATENT DOCUMENTS

| | | | |
|---|---|---|---|
| 2,194,958 | 3/1940 | Szegvari et al. | 260/759 |
| 2,262,770 | 11/1941 | La Piana | 260/6 |
| 2,262,771 | 11/1941 | La Piana | 260/6 |
| 2,310,795 | 2/1943 | La Piana et al. | 106/146 |
| 2,331,715 | 10/1943 | Nadeau et al. | 117/37 |
| 2,399,084 | 4/1946 | Watson | 260/8 |
| 2,453,752 | 11/1948 | La Piana et al. | 260/6 |
| 2,858,238 | 10/1958 | Brown, Jr. | 117/164 |
| 2,979,422 | 4/1961 | Bersin et al. | 117/106 |
| 3,016,599 | 1/1962 | Perry, Jr. | 28/78 |
| 3,076,720 | 2/1963 | Rice et al. | |
| 3,104,154 | 9/1963 | Morimoto et al. | 18/54 |
| 3,188,233 | 6/1965 | Powers et al. | 117/140 |
| 3,202,748 | 8/1965 | Nake et al. | 264/194 |
| 3,341,394 | 9/1967 | Kinney | 161/72 |
| 3,355,322 | 11/1967 | Newport et al. | 117/140 |
| 3,494,775 | 2/1970 | Cosia et al. | 106/124 |
| 3,655,862 | 4/1972 | Dorschner et al. | 264/290 |
| 3,690,925 | 9/1972 | Morris | 117/76 T |
| 3,692,618 | 9/1972 | Dorschner et al. | 161/72 |
| 3,704,198 | 11/1972 | Prentice | 161/148 |
| 3,705,068 | 12/1972 | Dobo et al. | 156/441 |
| 3,754,117 | 8/1973 | Walter | 219/383 |
| 3,755,527 | 8/1973 | Keller et al. | 264/210 |
| 3,762,928 | 10/1973 | Willems | 96/114.5 |

(List continued on next page.)

FOREIGN PATENT DOCUMENTS

| | | |
|---|---|---|
| 538901 | 4/1957 | Canada . |
| 0199171 | 10/1986 | European Pat. Off. . |
| 2364524 | 7/1974 | Germany . |
| 3 536 318 | 4/1987 | Germany . |
| 4108170 | 9/1992 | Germany . |
| 39-90 | 1/1964 | Japan . |
| 42-16065 | 9/1967 | Japan . |
| 45-34390 | 11/1970 | Japan . |
| 45-34391 | 11/1970 | Japan . |
| 49-48590 | 12/1974 | Japan . |
| 50-71700 | 6/1975 | Japan . |
| 07170904 | 10/1982 | Japan . |

(List continued on next page.)

OTHER PUBLICATIONS

PCT Search Report for PCT/US96/02072 dated Jul. 19, 1996.

Derwent WPI abstract for DE 35 36 318 dated Sep. 10, 1987.

Abstract JP, A, 04 136 268, Derwent Publications Ltd., London, GB, May 11, 1992.

Textile Research Journal, "Effect of Quaternized Amphiphilic Peptides on Pilling and Electrostatic Discharge of Wool Fabrics", vol. 64, No. 11, Nov. 1, 1994, pp. 648–652.

Theodoe H. Meltzer, Filtration in the Pharmaceutical Industry, Marcel Dekker, Inc., New York, 1987, pp. 310–314.

Zaverio M. Ruggeri, "Mechanisms of Shear–induced Platelet Adhesion and Aggregation," Thrombosis and Haemostasis–Journal of the International Society of Thrombosis and Haemostatasis, Jul. 1, 1993, Schattauer Stuttgart, New York, 1993, pp. 119–223.

V.A. Wente "Superfine Thermoplastic Fibers", Industrial and Engineering Chemistry, vol. 48, No. 8, pp. 1342–1346 (1956).

V.A. Wente, et al., "Manufacture of Superfine Organic Fibers" Navy Research Lab., Washington, D.C. NRL Rpt. 4364 (111437), Dtd May 25, 1954, U.S. Dept. of Commerce, Office of Technical Svcs.

R.R. Butin, et al., "Melt–Blowing—A One–Step Web Process for New Nonwoven Products", Journal of the Technical Association of the Pulp and Paper Industry, vol. 56, No. 4, pp. 74–77 (1973).

A.W. Adamson, Chapter XIII ("Wetting, Flotation, and Detergency") in Physical Chemistry of Surfaces, 5$^{th}$ Ed. Jogn Wiley & Sons, Inc., New York, N.Y., 1990, pp. 435–436.

Abstract JP 62–43000

Primary Examiner—John G. Weiss
Assistant Examiner—Dennis Ruhl
Attorney, Agent, or Firm—William E. Maycock

[57] ABSTRACT

A wettable article consisting of an article with a hydrophobic surface having a coating which includes a surface free energy modifier and a surface-active agent. The hydrophobic surface may include a hydrophobic polymer. The surface free energy modifier has a surface free energy greater than that of the surface of the article, but less than the surface tension of an aqueous liquid to which the wettable coated article may be exposed. The surface free energy modifier desirably is present in an amount sufficient to substantially cover the surface of the article. The surface-active agent is present in an amount effective to lower the surface tension of the liquid to a value which is greater than the surface free energy of the surface of the article and equal to or less than the surface free energy of the surface free energy modifier. The article desirably is a film or a fibrous web, such as a nonwoven web. Methods of preparing the wettable article also are described.

19 Claims, No Drawings

U.S. PATENT DOCUMENTS

| | | | |
|---|---|---|---|
| 3,781,414 | 12/1973 | Huber | 424/12 |
| 3,798,208 | 3/1974 | Miller | 260/119 |
| 3,802,817 | 4/1974 | Matsuki et al. | 425/66 |
| 3,849,241 | 11/1974 | Buntin et al. | 161/169 |
| 3,853,651 | 12/1974 | Porte | 156/73.6 |
| 3,966,580 | 6/1976 | Janata et al. | 204/195 |
| 3,978,185 | 8/1976 | Buntin et al. | 264/93 |
| 4,007,089 | 2/1977 | Smith, III | 195/68 |
| 4,064,605 | 12/1977 | Akiyama et al. | 28/103 |
| 4,066,512 | 1/1978 | Lai et al. | 195/127 |
| 4,091,140 | 5/1978 | Harmon | 428/288 |
| 4,100,319 | 7/1978 | Schwartz | 428/171 |
| 4,100,324 | 7/1978 | Anderson et al. | 428/288 |
| 4,118,531 | 10/1978 | Hauser | 428/224 |
| 4,263,180 | 4/1981 | Marconi et al. | 260/8 |
| 4,340,563 | 7/1982 | Appel et al. | 264/518 |
| 4,405,297 | 9/1983 | Appel et al. | 425/72 |
| 4,434,204 | 2/1984 | Hartman et al. | 428/198 |
| 4,539,294 | 9/1985 | Metcalfe et al. | 435/180 |
| 4,627,811 | 12/1986 | Greiser et al. | 425/72 |
| 4,644,045 | 2/1987 | Fowells | 526/348 |
| 4,657,873 | 4/1987 | Gadow et al. | 436/532 |
| 4,663,220 | 5/1987 | Wisneski et al. | 428/221 |
| 4,722,917 | 2/1988 | Seno et al. | 502/7 |
| 4,757,014 | 7/1988 | Hendrickson et al. | 435/180 |
| 4,761,161 | 8/1988 | Potschke | 8/543 |
| 4,816,177 | 3/1989 | Nelson et al. | 252/181 |
| 4,855,234 | 8/1989 | Hendrickson et al. | 435/181 |
| 4,906,616 | 3/1990 | Gilchrist et al. | 514/21 |
| 5,028,332 | 7/1991 | Ohnishi | 210/500.34 |
| 5,037,410 | 8/1991 | Zimmerman et al. | 604/373 |
| 5,043,278 | 8/1991 | Nagaoka et al. | 435/181 |
| 5,055,316 | 10/1991 | Hoffman et al. | 427/2 |
| 5,102,738 | 4/1992 | Bell et al. | 428/411.1 |
| 5,139,881 | 8/1992 | Henis et al. | 424/488 |
| 5,151,321 | 9/1992 | Reeves et al. | 428/286 |
| 5,208,075 | 5/1993 | Kroner et al. | 427/389.9 |
| 5,229,172 | 7/1993 | Cahalan et al. | 427/536 |
| 5,260,396 | 11/1993 | Kroner et al. | 527/201 |
| 5,270,384 | 12/1993 | Chang et al. | 525/54.1 |
| 5,284,910 | 2/1994 | Chang et al. | 515/54.1 |
| 5,284,911 | 2/1994 | Chang et al. | 525/54.1 |
| 5,310,885 | 5/1994 | Maier et al. | 530/413 |
| 5,344,560 | 9/1994 | Sugo et al. | 210/500.23 |
| 5,364,907 | 11/1994 | Rolando et al. | 525/54.1 |
| 5,455,108 | 10/1995 | Quincy et al. | 428/266 |
| 5,494,744 | 2/1996 | Everhart et al. | |
| 5,858,503 | 1/1999 | Everhart et al. | |

FOREIGN PATENT DOCUMENTS

| | | |
|---|---|---|
| 2043-000 | 8/1985 | Japan . |
| 3-111453 | 5/1991 | Japan . |
| 425689 | 3/1935 | United Kingdom . |
| 610 168 | 10/1948 | United Kingdom . |
| 1 374 663 | 11/1974 | United Kingdom . |
| 87-00561 | 1/1987 | WIPO . |
| 90/04609 | 5/1990 | WIPO . |
| 96/28602 | 9/1996 | WIPO . |

WETTABLE ARTICLE

This application is a continuation of application Ser. No. 08/404,004 entitled "Wettable Article" and filed in the U.S. Patent and Trademark Office on March 14, 1995 now abandoned. The entirety of this application is hereby incorporated by reference.

BACKGROUND OF THE INVENTION

The present invention relates to an article, such as a film or a fibrous web.

Polymers are used extensively to make a variety of products which include blown and cast films, extruded sheets, injection molded articles, foams, blow molded articles, extruded pipe, monofilaments, and nonwoven webs. Some of such polymers, such as polyolefins, are naturally hydrophobic, and for many uses this property is either a positive attribute or at least not a disadvantage.

There are a number of uses for polymers, however, where their hydrophobic nature either limits their usefulness or requires some effort to modify the surface characteristics of the articles made therefrom. By way of example, polyolefins, such as polyethylene and polypropylene, are used to manufacture polymeric fabrics which are employed in the construction of such disposable absorbent articles as diapers; incontinent care products; feminine care products, such as sanitary napkins and tampons; filter elements; wipes; surgical gowns and drapes; protective pads; wound dressings, such as bandages; and the like. Such polymeric fabrics often are nonwoven webs prepared by, for example, such processes as meltblowing, coforming, and spunbonding. Frequently, such polymeric fabrics need to be wettable by water. Wettability can be obtained by spraying or otherwise coating (i.e., surface treating or topically treating) the fabric with a surfactant solution during or after its formation, and then drying the web.

Some of the more common topically applied surfactants are nonionic surfactants, such as polyethoxylated octylphenols and condensation products of propylene oxide with propylene glycol, by way of illustration only. These surfactants are effective in rendering normally hydrophobic polymeric fabrics wettable. However, the surfactant is readily removed from the fabric, often after only a single exposure to an aqueous liquid.

Substantial efforts have been directed to increasing the durability of surfactants which are topically applied to a polymeric fabric. Such efforts include the following, by way of illustration:

(1) use of a composition which includes water, a primary surfactant, and a cosurfactant which is functional to wet the fabric with the composition and which provides for substantially uniform distribution of the primary surfactant onto the polymeric fabric;

(2) use of a surfactant, with or without a nonionic cosurfactant, which is the reaction product of an acid anhydride derivative, such as a substituted succinic anhydride, with a polyhydroxy compound, such as sorbitol, a polyethylene glycol, triethanolamine, a polyhydroxyamine, certain primary and secondary amines, and certain unsaturated aliphatic sulfo compounds;

(3) use of a surfactant, with or without a nonionic cosurfactant, which is the reaction product of certain unsaturated aliphatic sulfo compounds with the reaction product of an acid anhydride derivative, such as a substituted succinic anhydride, with a polyamine having at least one NH group capable of addition to a double bond;

(4) use of a surfactant mixture which includes an ester-acid, ester salt, or a mixture thereof, and an amidic-acid, amidic salt, or mixture thereof, with or without a nonionic cosurfactant; and (5) use of a surfactant mixture which includes a sorbitol succinate surfactant, such as an ethoxylated amino sorbitol succinate salt or an alkenyl succinate anhydride ethoxylated fatty amine salt, and a cowetting aid which can be, for example, a silicone polyether or a primary or secondary alcohol having up to about 8 carbon atoms.

In addition to water wettability, many absorbent, i.e., porous, products are concerned with, at least to some degree, the rate at which the aqueous liquid penetrates the porous product. For example, when the porous product is a non-woven web or other fibrous material, the liquid must penetrate between the fibers of the web. A porous substrate in which an aqueous liquid penetrates at a rapid rate will be more effective in absorbing large volumes of liquid delivered over a short period of time, and, as a consequence, more effective in preventing or minimizing leakage. Furthermore, a porous substrate which quickly absorbs liquid will allow other components of an absorbent product to more effectively move liquid away from the locus of liquid insult to the remainder of the absorbent product. Therefore, more of the absorbent product will be available for absorption of the liquid.

It is known that the rate of penetration of a liquid into a porous substrate is directly proportional to the surface tension of the liquid and the cosine of the contact angle that the liquid makes with the surface of the substrate (see, e.g., A. W. Adamson, Chapter XIII, "Wetting, Flotation, and Detergency" in "Physical Chemistry of Surfaces," Fifth Edition, John Wiley & Sons, New York, 1990, pp. 495–496). Lowering the surface tension of the liquid, therefore, has an adverse effect on the rate of liquid penetration. That is, when the surface tension of the liquid is decreased, the driving force of liquid penetration also is decreased. The cosine of the contact angle, on the other hand, is at a maximum value of 1 when the contact angle is zero. As the contact angle increases, the cosine decreases, approaching zero as the contact angle approaches 90°.

The methods of making a polymeric substrate wettable as described above all involve reducing the surface tension of the liquid to a value which is approximately the same as or lower than the surface free energy of the substrate to be wetted by the liquid. Such methods also lower the contact angle. However, as already noted, lowering both the surface tension of the liquid and the contact angle is counterproductive with respect to the rate of liquid penetration. Thus, there is a need for materials which are wettable and exhibit a rapid uptake of liquid.

SUMMARY OF THE INVENTION

The present invention addresses some of the difficulties and problems discussed above by providing a wettable article which also has a rapid rate of liquid penetration. Wettability and rapid liquid penetration properties are achieved by minimizing the reduction in the surface tension of an aqueous liquid coming in contact with the article while maintaining a small contact angle that the liquid makes with the surface of the article.

Accordingly, the present invention provides a wettable article consisting of an article with a hydrophobic surface having a coating which includes a surface free energy modifier and a surface-active agent. The hydrophobic surface may be composed of a hydrophobic polymer. The surface free energy modifier has a surface free energy greater than that of the surface of the article, but less than the surface tension of an aqueous liquid to which the wettable article may be exposed, and desirably is present in an amount sufficient to substantially cover the surface of the article. The surface-active agent is present in an amount effective to lower the surface tension of the liquid to a value which is greater than the surface free energy of the surface of the article and equal to or less than the surface free energy of the surface free energy modifier.

The article may be, by way of example only, a film or a fibrous sheet. The fibrous sheet may be a woven or nonwoven web.

The hydrophobic polymer may be, by way of example, a polyolefin. Typical polyolefins are polyethylene and polypropylene. Also by way of example, the surface free energy modifier may be a protein and the surface-active agent may be a polyethoxylated alkylphenol.

The present invention also provides a method of preparing a wettable article. The method involves forming an article by melt extrusion, at least a portion of which is formed from a polymeric composition which includes a hydrophobic polymer and a surface-active agent adapted to migrate to a surface of the article; and coating the surface of the article with a surface free energy modifier.

By way of example, the surface free energy modifier may have a surface free energy greater than that of the surface of the article, but less than the surface tension of an aqueous liquid to which the wettable article may be exposed. As another example, the surface free energy modifier may be present in an amount sufficient to substantially cover the surface of the article.

The method may include the additional step of causing the surface-active agent to migrate to the surface of the article in an amount effective to lower the surface tension of the liquid to a value which is greater than the surface free energy of the surface of the article and equal to or less than the surface free energy of the surface free energy modifier.

The present invention further provides a method of preparing a wettable article which involves forming an article by melt extrusion, wherein the article has a hydrophobic surface; coating the surface of the article with a surface free energy modifier; and treating the coated article with a surface-active agent. For example, the surface free energy modifier may have a surface free energy greater than that of the surface of the article, but less than the surface tension of an aqueous liquid to which the wettable article may be exposed. As another example, the surface-active agent may be present in an amount effective to lower the surface tension of the liquid to a value which is greater than the surface free energy of the surface of the article and equal to or less than the surface free energy of the surface free energy modifier.

The wettable article of the present invention may be employed as a component of a disposable absorbent product. The disposable absorbent product may be, for example, a diaper, a feminine care product, or an incontinent product.

DETAILED DESCRIPTION OF THE INVENTION

As used herein, the terms "article" and "product" are synonyms and are meant to include any article or product which is formed by a melt-extrusion process, regardless of the size or shape of the article. As a practical matter, the present disclosure is directed primarily to melt-extruded films, fibers, and nonwoven webs comprised of such fibers. Nevertheless, other articles or products are deemed to come within the spirit and scope of the present invention.

In those embodiments in which the article is a nonwoven web, such nonwoven web in general can be prepared by any of the means known to those having ordinary skill in the art. For example, the nonwoven web can be prepared by such processes as meltblowing, coforming, spunbonding, hydroentangling, carding, air-laying, and wet-forming.

The nonwoven web more typically will be a nonwoven web prepared by meltblowing, coforming, spunbonding, and the like. By way of illustration only, such processes are exemplified by the following references which are incorporated herein by reference:

(a) meltblowing references include, by way of example, U.S. Pat. No. 3,016,599 to R. W. Perry, Jr., U.S. Pat. No. 3,704,198 to J. S. Prentice, U.S. Pat. No. 3,755,527 to J. P. Keller et al., U.S. Pat. No. 3,849,241 to R. R. Butin et al., U.S. Pat. No. 3,978,185 to R. R. Butin et al., and U.S. Pat. No. 4,663,220 to T. J. Wisneski et al. See, also, V. A. Wente, "Superfine Thermoplastic Fibers", *Industrial and Engineering Chemistry*, Vol. 48, No. 8, pp. 1342–1346 (1956); V. A. Wente et al., "Manufacture of Superfine Organic Fibers", Navy Research Laboratory, Washington, D.C., NRL Report 4364 (111437), dated May 25, 1954, United States Department of Commerce, Office of Technical Services; and Robert R. Butin and Dwight T. Lohkamp, "Melt Blowing—A One-Step Web Process for New Nonwoven Products", *Journal of the Technical Association of the Pulp and Paper Industry*, Vol. 56, No.4, pp. 74–77 (1973);

(b) coforming references include U.S. Pat. No. 4,100,324 to R. A. Anderson et al. and U.S. Pat. No. 4,118,531 to E. R. Hauser; and (c) spunbonding references include, among others, U.S. Pat. No. 3,341,394 to Kinney, U.S. Pat. No. 3,655,862 to Dorschner et al., U.S. Pat. No. 3,692,618 to Dorschner et al., U.S. Pat. No. 3,705,068 to Dobo et al., U.S. Pat. No. 3,802,817 to Matsuki et al., U.S. Pat. No. 3,853,651 to Porte, U.S. Pat. No. 4,064,605 to Akiyama et al., U.S. Pat. No. 4,091,140 to Harmon, U.S. Pat. No. 4,100,319 to Schwartz, U.S. Pat. No. 4,340,563 to Appel and Morman, U.S. Pat. No. 4,405,297 to Appel and Morman, U.S. Pat. No. 4,434,204 to Hartman et al., U.S. Pat. No. 4,627,811 to Greiser and Wagner, and U.S. Pat. No. 4,644,045 to Fowells.

The term "hydrophobic polymer" is used herein to mean any polymer resistant to wetting, or not readily wet, by water, i.e., having a lack of affinity for water. A hydrophobic polymer typically will have a surface free energy of about 40 dynes/cm ($40 \times 10^{-5}$ newtons/cm or N/cm) or less. Examples of hydrophobic polymers include, by way of illustration only, polyolefins, such as polyethylene, poly(isobutene), poly(isoprene), poly(4-methyl-1-pentene), polypropylene, ethylene-propylene copolymers, ethylene-propylene-hexadiene copolymers, and ethylene-vinyl acetate copolymers; styrene polymers, such as poly(styrene), poly(2-methylstyrene), styrene-acrylonitrile copolymers having less than about 20 mole-percent acrylonitrile, and styrene-2,2,3,3,-tetrafluoropropyl methacrylate copolymers; halogenated hydrocarbon polymers, such as poly (chlorotrifluoroethylene), chlorotrifluoroethylene-tetrafluoroethylene copolymers, poly(hexafluoropropylene), poly(tetrafluoroethylene), tetrafluoroethylene-ethylene copolymers, poly(trifluoroethylene), poly(vinyl fluoride), and poly(vinylidene fluoride); vinyl polymers, such as poly(vinyl butyrate), poly(vinyl decanoate), poly(vinyl dodecanoate), poly(vinyl hexadecanoate), poly(vinyl hexanoate), poly(vinyl propionate), poly(vinyl octanoate), poly(heptafluoroisopropoxyethylene), 1-heptafluoroisopropoxymethylethylene-maleic acid copolymers, poly(heptafluoroisopropoxypropylene), poly(methacrylonitrile), poly(vinyl alcohol), poly(vinyl butyral), poly(ethoxyethylene), poly(methoxyethylene), and poly(vinyl formal); acrylic polymers, such as poly(n-butyl acetate), poly(ethyl acrylate), poly[(1-chlorodifluoromethyl) tetrafluoroethyl acrylate], poly[di(chlorofluoromethyl) fluoromethyl acrylate], poly(1,1-dihydroheptafluorobutyl acrylate), poly(1,1-dihydropentafluoroisopropyl acrylate), poly(1,1-dihydropentadecafluorooctyl acrylate), poly(heptafluoroisopropyl acrylate), poly[5-(heptafluoroiospropoxy)pentyl acrylate], poly[11-(heptafluoroiospropoxy)undecyl acrylate], poly[2-(heptafluoropropoxy)ethyl acrylate], and poly(nonafluoroisobutyl acrylate); methacrylic polymers, such as poly(benzyl methacrylate), poly(n-butyl methacrylate), poly(isobutyl methacrylate), poly(t-butyl methacrylate), poly(t-butylaminoethyl methacrylate), poly(dodecyl methacrylate), poly(ethyl methacrylate), poly(2-ethylhexyl methacrylate), poly(n-hexyl methacrylate), poly(dimethylaminoethyl methacrylate), poly(hydroxyethyl methacrylate), poly(phenyl methacrylate), poly(n-propyl methacrylate), poly(octadecyl methacrylate), poly(1,1-dihydropentadecafluorooctyl methacrylate), poly(heptafluoroisopropyl methacrylate), poly(heptadecafluorooctyl methacrylate), poly(1-hydrotetrafluoroethyl methacrylate), poly(1,1-dihydrotetrafluoropropyl methacrylate), poly(1-hydrohexafluoroisopropyl methacrylate), and poly(t-nonafluorobutyl methacrylate); polyethers, such as poly(chloral), poly(oxybutene)diol, poly(oxyisobutene)diol, poly(oxydecamethylene), poly(oxyethylene)-dimethyl ether polymers having molecular weights below about 1,500, poly(oxyhexamethylene)diol, poly(oxypropylene)diol, poly(oxypropylene)-dimethyl ether, and poly(oxytetramethylene); polyether copolymers, such as poly(oxyethylene)-poly(oxypropylene)-poly(oxyethylene) block copolymers, oxyethylene-oxypropylene copolymers having greater than about 20 mole percent oxypropylene, oxytetramethylene-oxypropylene copolymers, and block copolymers having oxyethylene-oxypropylene copolymer blocks separated by a poly(oxydimethylsilylene) block; polyamides, such as poly[imino(1-oxodecamethylene)], poly[imino(1-oxododecamethylene)] or nylon 12, poly[imino(1-oxohexamethylene)] or nylon 6, poly[imino(1-oxotetramethyl-ene)] or nylon 4, poly(iminoazelaoyliminononamethylene), poly(iminosebacoyliminodecamethylene), and poly(iminosuberoyliminooctamethylene); polyimines, such as poly[(benzoylimino)ethylene], poly[(butyrylimino)ethylene], poly[(dodecanoylimino)ethylene], (dodecanoylimino)ethylene-(acetylimino)trimethylene copolymers, poly[(heptanoylimino)ethylene], poly[(hexanoylimino)ethylene], poly{[(3-methyl)butyrylimino]ethylene}, poly[(pentadecafluorooctadecanoylimino)ethylene], and poly[(pentanoylimino)ethylene]; polyurethanes, such as those prepared from methylenediphenyl diisocyanate and butanediol poly(oxytetramethylene) diol, hexamethylene diisocyanate and triethylene glycol, and 4-methyl-1,3-phenylene diisocyanate and tripropylene glycol; polysiloxanes, such as poly(oxydimethylsilylene) and poly(oxymethylphenylsilylene); and cellulosics, such as amylose, amylopectin, cellulose acetate butyrate, ethyl cellulose, hemicellulose, nitrocellulose, and starch.

As stated earlier, the wettable article of the present invention includes an article having a surface composed of a hydrophobic polymer. Thus, the term "surface" is used herein to mean that portion of the total surface area of the article which is composed of a hydrophobic polymer. The surface of the article may encompass the entire surface area of the article or only a portion thereof. For example, when the article is a nonwoven web, the fibers of which the web is composed may be prepared from a single hydrophobic polymer. Alternatively, such fibers may be bicomponent fibers, in which one component is a hydrophobic polymer and the other component is a different hydrophobic polymer or a nonhydrophobic polymer, e.g., a hydrophilic polymer. The fibers may be sheath-core bicomponent fibers, in which case the sheath typically would be composed of a hydrophobic polymer. The fibers also may be side-by-side bicomponent fibers. Moreover, the fibers of which the nonwoven web is composed may have a circular or a noncircular cross-section. The fibers also may be polycomponent fibers, provided at least one component is a hydrophobic polymer.

The surface of the article of the present invention has a coating thereon. The coating includes a surface free energy modifier and a surface-active agent. The surface free energy modifier has a surface free energy greater than that of the surface of the article, but less than the surface tension of an aqueous liquid to which the wettable coated article may be exposed, and is present in an amount sufficient to substantially cover the surface of the article. That is, the surface of the article is covered with the surface free energy modifier to an extent such that the surface free energy of the portion of the article upon which the liquid impinges is the surface free energy of the surface free energy modifier, rather than the surface free energy of the hydrophobic polymer.

The surface free energy modifier may be any material which has a surface free energy greater than that of the surface of the article, but less than the surface tension of an aqueous liquid to which the wettable coated article may be exposed. Desirably, the surface free energy modifier will not be removed readily by the liquid environment. For example, when the hydrophobic polymer of which the surface is composed is a polyolefin, such as polypropylene, the surface free energy modifier may be a protein. The protein desirably will have a weight average molecular weight of at least about 10,000 Daltons. Examples of such proteins include, by way of illustration only, fibrinogen, such as baboon plasma fibrinogen, bovine plasma fibrinogen; cat plasma fibrinogen, dog plasma fibrinogen, goat plasma fibrinogen, guinea pig plasma fibrinogen, horse plasma fibrinogen, human plasma fibrinogen, mouse plasma fibrinogen, pig plasma fibrinogen, rabbit plasma fibrinogen, rat plasma fibrinogen, and sheep plasma fibrinogen; albumin, such as baboon albumin, bovine albumin, cat albumin, chicken albumin, chicken egg albumin, dog albumin, goat albumin, guinea pig albumin, hamster albumin, horse albumin, human albumin, mouse albumin, pig albumin, rabbit albumin, rat albumin, rhesus monkey albumin, sheep albumin, turkey albumin, and turkey egg albumin; casein, such as bovine milk casein, goat milk casein, human milk casein, sheep milk casein, and α-, β- and kappa-casein from bovine milk; hemoglobin, such as baboon hemoglobin, bovine hemoglobin, cat hemoglobin, dog hemoglobin, garter snake hemoglobin, goat hemoglobin, horse hemoglobin, human hemoglobin, mouse hemoglobin, pig hemoglobin, pigeon hemoglobin, rabbit hemoglobin, rat hemoglobin, sheep hemoglobin, and tukey hemoglobin; and lysozyme, such as chicken egg white lysozyme, human milk lysozyme, and turkey egg white lysozyme.

The surface of the article may be coated with the surface free energy modifier by any known means. For example, the surface free energy modifier may be simply adsorbed onto the surface of the article. As another example, the surface free energy modifier may be covalently bonded to the surface. As still another example, the surface of the article may be modified to assist or enhance either adsorption or covalent bonding. Thus, the surface may be exposed to a corona or plasma field or to electron beam or other ionizing radiation to aid either the adsorption or covalent bonding of the surface free energy modifier to the surface of the article; see, for example, U.S. Pat. No. 4,238,291 to Lowther, U.S. Pat. No. 3,754,117 to Walter, and U.S. Pat. No. 5,102,738 to Bell et al., each of which is incorporated herein by reference.

The term "surface-active agent" is used herein with its usual meaning and includes a single surface-active agent or a mixture of two or more surface-active agents. If a mixture of two or more surface-active agents is employed, the agents may be selected from the same or different classes, provided only that the agents present in the mixture are compatible with each other.

In general, the surface-active agent is present in the coating in an amount effective to lower the surface tension of the liquid to a value which is greater than the surface free energy of the surface of the article and equal to or less than the surface free energy of the surface free energy modifier.

The surface-active agent may be any surface active agent known to those having ordinary skill in the art, including anionic, cationic, and nonionic surfactants. Examples of anionic surfactants include, among others, linear and branched-chain sodium alkylbenzenesulfonates, linear and branched-chain alkyl sulfates, and linear and branched-chain alkyl ethoxy sulfates. Cationic surfactants include, by way of illustration, tallow trimethylammonium chloride. Examples of nonionic surfactants, include, again by way of illustration only, alkyl polyethoxylates; polyethoxylated alkylphenols; fatty acid ethanol amides; polysiloxane polyethers; and complex polymers of ethylene oxide, propylene oxide, and alcohols. Desirably, the surfactant will be a nonionic surfactant.

One method of the present invention for preparing a wettable article involves forming an article by melt extrusion, at least a portion of which is formed from a polymeric composition which includes a hydrophobic polymer and a surface-active agent adapted to migrate to the surface of the article. The presence of surface-active agent on the surface of the article immediately after its formation is acceptable, provided that (a) such presence does not significantly adversely interfere with the coating of the surface with a surface free energy modifier, described hereinafter, and (b) the coating of the surface with a surface free energy modifier results in a wettable article as defined herein. Desirably, migration of the surface-active agent takes place only after a migration-inducing, post-formation event, as described hereinafter.

The amount of surface-active agent included in the hydrophobic polymer may vary over a wide range. For example, the surface-active agent may be present in an amount of from about 0.01 to about 3 percent by weight, based on the hydrophobic polymer. As a further example, the surface-active agent may be present in an amount of from about 0.01 to about 1 percent by weight, based on the hydrophobic polymer. As still another example, when the surface-active agent is a polyethoxylated alkylphenol, the surface-active agent typically will be present in an amount of from about 0.05 to about 0.4 percent by weight, based on the hydrophobic polymer. Notwithstanding the foregoing ranges, the use of any amount of surface-active agent which results in a wettable surface is deemed to come within the scope of the present invention, provided that (a) the surface-active agent present on the surface does not significantly adversely interfere with the coating of the surface with a surface free energy modifier or (b) an amount of surface-active agent remains in the hydrophobic polymer which may be induced to migrate to the surface as described herein. If the presence of surface-active agent on the surface significantly interferes with the coating of the surface with a surface free energy modifier, the agent may be removed by, for example, washing the article with water before a coating procedure is carried out.

As noted above, the surface of the article is coated with a surface free energy modifier having a surface free energy greater than that of the surface of the article, but less than the surface tension of an aqueous liquid to which the wettable coated article may be exposed, in an amount sufficient to substantially cover the surface of the article. The coating may be applied by means which are well known to those having ordinary skill in the art, depending upon the nature of the modifier. For example, the surface may be coated with a protein by a simple topical treatment, such as dipping, spraying, brushing, direct and offset gravure printing, and doctor blading.

In the event the coating step removes the surface-active agent from the surface of the article, or the wettable article of the present invention does not result from the coating step, an additional step may be employed. The additional step involves causing the surface-active agent by a migration-inducing, post-formation event to migrate to the surface of the article in an amount effective to lower the surface tension of the liquid to a value which is greater than the surface free energy of the surface of the article and equal to or less than the surface free energy of the surface free energy modifier. An example of such a post-formation event is the coating of the surface with the surface free energy modifier, e.g., a protein. However, the migration of the surface-active agent after coating the surface is not rapid, and may require days or even weeks or months at ambient temperature (i.e., 20°–25° C.). The migration may be expedited by heating the coated article at a temperature up to the temperature at which either the surface free energy modifier or the article begins to degrade. The time the coated article is heated depends on the temperature, with heating time being inversely proportional to the heating temperature. For example, the coated article may be heated at a temperature of from about 50° C. to about 100° C. for from about 30 minutes to about 10 hours.

Another method of the present invention for preparing a wettable article involves forming an article by melt extrusion, in which the article has a surface consisting of a hydrophobic polymer. The surface of the article is coated with a surface free energy modifier having a surface free energy greater than that of the surface of the article, but less than the surface tension of an aqueous liquid to which the wettable coated article may be exposed, in an amount sufficient to substantially cover the surface of the article. The coated article then is treated with a surface-active agent in an amount effective to lower the surface tension of the liquid to a value which is greater than the surface free energy of the surface of the article and equal to or less than the surface free energy of the surface free energy modifier.

The present invention is further described by the examples which follow. Such examples, however, are not to be construed as limiting in any way either the spirit or the scope of the present invention. The water employed in the examples was distilled, deionized water having an uncorrected surface tension of 72.5 dynes/cm ($72.5 \times 10^{-5}$ newtons/cm) as determined by means of a Fisher Scientific Surface Tensiometer 20 using a platinum-iridium du Nouy ring (Fisher Scientific Company, Pittsburgh, Pa.).

EXAMPLE 1

Two types of a polypropylene spunbonded nonwoven web were prepared essentially as described in U.S. Pat. No. 3,802,817 to Matsuki; each web had a basis weight of 0.8 ounces per square yard or osy (about 27 grams per square meter or gsm). The first, referred to herein as Web A, was prepared from polypropylene which contained 0.13 percent by weight, based on the weight of polypropylene, of internally added surface-active agent, Triton® X-102 (Rohm and Haas Co., Philadelphia, Pa.). The second, Web B, did not contain internally added surfactant, but was otherwise identical to Web A. Each web was cut into samples 7 inches cross direction (CD) by 10 inches machine direction (MD) (about 18 cm CD×25 cm MD). Samples of each web were soaked individually for 7.5 minutes in 500 ml aliquots of 20 mM pH 7 sodium phosphate buffer containing 0.2 mg of bovine fibrinogen source as supplied (Fraction I, Type IV, 58 percent protein, Catalog No. F4753, Sigma Chemical Company, St. Louis, Mo.) per ml of buffer. The soaked samples were identified as 1A1 and 1B1, respectively. Two samples were soaked per 500 ml aliquot and a total of eight samples were prepared. One sample of each web was additionally rinsed in water for 10 to 30 seconds, then passed through an Atlas Laboratory Wringer with a 30-lb (13.6-kg) nip setting (Atlas Electric Devices Company, Chicago, Ill.); the samples were identified as 1A2 and 1B2, respectively. Another sample of each web was nipped following the fibrinogen soak, then rinsed in water and nipped a second time and identified as 1A3 and 1B3, respectively. Samples were hung in a fume hood to dry overnight. After drying, each sample was cut in half and one half hung in a 70° C. oven for about seven hours.

The critical surface tension of wetting (CSTW) for each sample, before and after heating, was determined by placing 3–6 drops of Politest surface tension liquids (Pillar Technologies, Hartland, Mich.) on each web. The web was deemed wettable if the drops spread significantly or penetrated the web within one minute. The surface tension of the Politest liquid which wet the web was recorded. When water was the test fluid, the degree of wettability was recorded. Wetting was deemed immediate if the penetration of all of the drops occurred in less than one second. Wetting was characterized as partial when some regions of the sample were wettable by water and other regions were not. The results are summarized in Table 1.

TABLE 1

Summary of CSTW Determinations

| Sample | CSTW before heating[a] | CSTW after heating[a] |
| --- | --- | --- |
| Web A | 36 | 37 |
| 1A1 | 58 | Immediately wettable |
| 1A2 | 58 | Immediately wettable |
| 1A3 | 58 | Immediately wettable |
| Web B | 36 | 36 |
| 1B1 | 58 | 40–50[b] |
| 1B2 | 58 | 40–50[b] |
| 1B3 | 56–64[b] | 40 |

[a]In dynes/cm ($10^{-5}$ newtons/cm).
[b]The sample was not wettable at the higher value, but was wettable at the lower value. Insufficient sample was available to test with Politest surface tension liquids having intermediate values.

It is apparent that the fibrinogen-coated samples prepared from Web A, which contained a small quantity of a surface-active agent, Triton® X-102, became water wettable upon heating, whereas fibrinogen-coated Web B samples (lacking the surface-active agent) did not become water wettable upon heating. Note that the fibrinogen, a surface free energy modifier, raised the surface free energy of the web from that of polypropylene (i.e., 36 dynes/cm or $36 \times 10^{-5}$ newtons/cm) to 58 dynes/cm or $58 \times 10^{-5}$ newtons/cm. Heating the fibrinogen-coated, surface-active agent-containing webs caused the surface-active agent to migrate to the surface of the web, thereby rendering the web wettable with water. However, in the absence of the surface free energy modifier, the surface-active agent did not migrate to the surface in an amount sufficient to render the web water wettable.

EXAMPLE 2

A 3-inch×3-inch (about 8-cm×8-cm) portion of Sample 1A1 from Example 1 was heated in a 70° C. oven for about 7 hours and identified as Sample 2A2. The sample then was soaked in 80 ml of distilled, deionized water for about 25 hours and identified as Sample 2A3. The sample was heated again in a 70° C. oven for about 7 hours and identified as Sample 2A4. Two small regions about 1 $cm^2$ in size were removed from the sample after each of the above procedures and subjected to electron spectroscopy for chemical analysis (ESCA). The ESCA data were collected by Evans East, Plainsboro, N.J. A sample of original Web A (described in Example 1) also was characterized by ESCA, and served as a control. The wettability of Sample 1A1 before and after each procedure (i.e., heat or soak) was evaluated as described in Example 1. The results are summarized in Table 2.

TABLE 2

Summary of CSTW and ESCA Determinations

| Sample | CSTW[a] | ESCA (atom % ratio) | |
| --- | --- | --- | --- |
|  |  | N/C | O/C |
| Web A | 36 | 0.00 | 0.03 |
| 1A1 | 58 | 0.17 | 0.30 |
| 2A2 | Immediately wet | 0.11 | 0.28 |
| 2A3 | 60 | 0.17 | 0.27 |
| 2A4 | Partially wet | 0.14 | 0.28 |

[a]In dynes/cm ($10^{-5}$ newtons/cm).

Web A, it will be remembered from Example 1, was made from polypropylene containing a small amount of a surface-active agent. Coating the web with fibrinogen (Sample 1A1) resulted in a web having a higher surface free energy, although the web still was not wettable with water. Sample 2A2, obtained by heating Sample 1A1, was immediately water wettable. Water wettability, however, was lost upon soaking the sample (Sample 2A3). Heating Sample 2A3 to give Sample 2A4 resulted in partial wettability.

It is apparent that the soaking step did not remove the fibrinogen coating from the web; compare the CSTW results for Samples 1A1 and 2A3, in which CSTW values of 58 and 60, respectively, were obtained. This conclusion also is supported by the ESCA data in which the N/C ratios for the two samples were the same. The N/C ratios also indicate the migration of surface-active agent to the surface after the first heating step (the change from 0.17 to 0.11 for Samples 1A1 and 2A2, respectively, suggests that the surface-active agent is associated with the fibrinogen coating), the removal of the agent by the soaking step (the change from 0.11 to 0.17 for Samples 2A2 and 2A3, respectively), and the migration of an additional but smaller amount of surface-active agent after the second heating step (the change from 0.17 to 0.14 for Samples 2A3 and 2A4, respectively).

EXAMPLE 3

The procedure of Example 2 was repeated, except that Sample 1A1 from Example 1 was replaced with Sample 1A3 from Example 1 (Sample 1A3 was a nonwoven web prepared from polypropylene containing an internally added surface-active agent and which had been treated with an aqueous fibrinogen solution, nipped, rinsed in water, and nipped again). The sample was heated in a 70° C. oven for about 7 hours, soaked in 80 ml distilled, deionized water (designated 3/1A3/h) for about 25 hours, air dried, heated again in a 70° C. oven for another 7 hours, and soaked a final time in a fresh 80 ml aliquot of distilled, deionized water (designated 3/1A3/hsh) for 24 hours. The surface tension of the soak water was measured before and after the fabric was soaked by means of a Fisher Scientific Surface Tensiometer 20 using a platinumiridium du Nouy ring (Fisher Scientific Company, Pittsburgh, Pa.).

A sample of Web A (described in Example 1) also was heated at 70° C. for 7 hours and then soaked for about 25 hours in water (designated Web A/h) to provide a control. Because Web A was not wettable by water, it was suspended below the surface of the water with a weight (steel nut). The surface tension of the soak water before and after the web was soaked was determined with the weight present.

The data are summarized in Table 3.

TABLE 3

Summary of Surface Tension Data

| | Surface Tension[a] | |
|---|---|---|
| Soak Water | Before Soak | After Soak |
| 3/1A3/h | 72.8 | 62.8 |
| 3/1A3/hsh | 72.4 | 70.2 |
| Web A/h | 72.5 | 70.8 |

[a]In dynes/cm ($10^{-5}$ newtons/cm).

The decrease in the soak water surface tension after Sample 1A3 and Web A were heated and soaked indicates that surface-active agent was present at the sample or web surfaces and dissolved in the soak water during the soaking process; see the results for soak water 3/1A 3/h and soak water Web/A/h, respectively. The results indicate that the fibrinogen coating on Sample 1A3 contributed to the increase migration of the surface-active agent to the surface of the sample when compared to Web A. Also, the surface tension data for the first and second soaks for Sample 1A3 suggest that less surface-active agent is available at the surface of the web after the second heating. This is consistent with the decrease in water wettability found after soaking and then heating Sample 1A1 for the second time as shown in Example 2 (see the results for Samples 2A2 and 2A4).

EXAMPLE 4

The procedure of Example 1 was repeated to produce fibrinogen-coated samples of Webs A and B. Web A was prepared from polypropylene which contained 0.13 percent by weight, based on the weight of polypropylene, of internally added surface-active agent, Triton® X-102. Web B did not contain internally added surfactant, but was otherwise identical to Web A. Each web was prepared essentially as described in U.S. Pat. No. 3,802,817 to Matsuki and each web had a basis weight of 0.8 osy (about 27 gsm). Each web was cut into samples 7 inches CD by 10 inches MD (about 18 cm CD×25 cm MD). Samples of each web were soaked individually for 5 minutes in 500 ml aliquots of 20 mM pH 7 sodium phosphate buffer containing 0.2 mg of bovine fibrinogen source as supplied (Fraction I, Type IV, 58 percent protein, Catalog No. F4753, Sigma Chemical Company, St. Louis, Mo.) per ml of buffer. The soaked samples were identified as 4A1 and 4B1, respectively. Each sample was air dried in a fume hood. The samples were stored (aged) at ambient temperature and the critical surface tension of wetting (CSTW) for each of Samples 4A1 and 4B1 was measured over time. Web A was included as a control. The results are summarized in Tables 4–6, inclusive.

TABLE 4

Effect of Aging on Sample 4A1

| Aging Period[a] | CSTW[b] | Water Wettability |
|---|---|---|
| 0 | N/D[c] | Not wettable |
| 2 | 64 | N/D |
| 15 | 70 | N/D |
| 30 | N/D | Partially wettable |
| 163 | N/D | Immediately wettable |

[a]In days.
[b]In dynes/cm ($10^{-5}$ newtons/cm).
[c]Not determined.

TABLE 5

Effect of Aging on Sample 4B1

| Aging Period[a] | CSTW[b] | Water Wettability |
|---|---|---|
| 1 | N/D[c] | Not wettable |
| 34 | N/D | Not wettable |
| 55 | N/D | Not wettable |
| 64 | 60 | Not wettable |

[a]In days.
[b]In dynes/cm ($10^{-5}$ newtons/cm).
[c]Not determined.

TABLE 6

Effect of Aging on Web A

| Aging period[a] | CSTW[b] | Water Wettability |
|---|---|---|
| 4 | N/D[c] | Not wettable |
| 11 | 36 | N/D |
| 12 | 36 | N/D |

[a]In months.
[b]In dynes/cm ($10^{-5}$ newtons/cm).
[c]Not determined.

This example demonstrates that aging produces the same result as heating, although much more slowly; that is, aging results in the slow migration of surface-active agent to the surface of the sample. Note the increase in surface free energy for Sample 4A1 over time and the associated improvement in water wettability. The migration of surface-active agent did not occur to an appreciable extent in the absence of the fibrinogen coating (compare Table 6 with Table 4). Finally, the data of Table 5 demonstrate that the fibrinogen coating alone does not age to produce a wettable surface.

EXAMPLE 5

The procedure of Example 1 was repeated, except that a number of different proteins, including fibrinogen, were employed and samples were air dried in a fume hood after being coated. The soaking period with the fibrinogen solution remained at 7.5 minutes, whereas for all other protein solutions a 60-minute soaking period was employed. The other proteins included in this example were bovine serum albumin (BSA), Catalog No. A3350; β-casein, Catalog No. C6905; lysozyme, Catalog No. L6876; casein acid hydrolysates, Catalog No. C9386, all from Sigma Chemical Company; and hemoglobin, Catalog No. 100714, from ICN Biomedicals, Inc., Irvine, Calif. Most of the coated samples were heated in a 70° C. oven for 7 hours. The critical surface tension of wetting (CSTW) for each sample, before and after heating, was determined as described in Example 1. The data are summarized in Table 7; the protein concentrations listed in the table are the amounts of protein source as supplied per ml of buffer.

TABLE 7

Summary of CSTW Determinations

| Web | Protein Type | Concn.[a] | CSTW Before heating[b] | After heating[b] |
|---|---|---|---|---|
| A | — | — | 36 | 36 |
| A | Fibrinogen | 0.2 | 58 | Immed. wet |
| A | BSA | 1.0 | 68 | Partially wet |
| A | BSA | 0.1 | N/D[c] | Partially wet |
| A | β-Casein | 1.0 | Partially wet | Partially wet |
| A | Hemoglobin | 0.2 | 60–66[d] | Immed. wet |
| A | Lysozyme | 1.0 | 68 | Partially wet |
| A | Casein hyd. | 1.0 | 40–50[d] | <40 |
| B | — | — | 36 | 36 |
| B | Fibrinogen | 0.2 | 56 | 40–44[d] |
| B | BSA | 1.0 | 58 | <40 |
| B | β-Casein | 1.0 | Partially wet | Not wettable |
| B | Hemoglobin | 0.2 | 60–66[d] | 40–50 |
| B | Lysozyme | 1.0 | 68 | 40 |
| B | Casein hyd. | 1.0 | 40 | <40 |

[a]In mg protein source per ml of buffer solution.
[b]In dynes/cm ($10^{-5}$ newtons/cm).
[c]Not determined.
[d]The sample was not wettable at the higher value, but was wettable at the lower value. Insufficient sample was available to test with Politest surface tension liquids having intermediate values.

All protein coatings on Web A, except β-casein and casein hydrolysates, became more water wettable after heating the coated web. The fibrinogen and hemoglobin coatings provided the most pronounced increase in web hydrophilicity.

EXAMPLE 6

Triton® X-102 was applied topically to Webs A and B, both as part of and subsequent to treatment of the webs with a fibrinogen solution as described in Example 1. Three different 0.2 mg/ml fibrinogen solutions were prepared with 20 mM pH 7 sodium phosphate buffer. The first (Solution A) contained only fibrinogen, the second (Solution B) also contained 0.04 percent by weight, based on the weight of the buffer solution, of Triton® X-102, and the third (Solution C) also contained 0.10 percent by weight, based on the weight of the buffer solution, of Triton® X-102. Samples of Webs A and B were soaked in each solution as described in Example 1, nipped without rinsing, and air dried in a fume hood. In addition, samples of Webs A and B and samples of fibrinogen-coated Webs A and B were soaked for 1 minute in water containing 0.12 percent by weight, based on the weight of the water, of Triton® X-102, (Solution D), nipped, and air dried in a fume hood. The critical surface tension of wetting (CSTW) for each sample was determined as described in Example 1. The data are summarized

TABLE 8

Summary of CSWT Determinations

| | Solution(s) Used | | | | | |
|---|---|---|---|---|---|---|
| Web | A | B | C | D | CSWT[a] | Water Wettability |
| A | — | X | — | — | <50 | Not wettable |
| A | — | — | X | — | <50 | Not wettable |
| A | X | — | — | — | 56–62[b] | Not wettable |

TABLE 8-continued

Summary of CSWT Determinations

| | Solution(s) Used | | | | | |
|---|---|---|---|---|---|---|
| Web | A | B | C | D | CSWT[a] | Water Wettability |
| A | X | — | — | X | N/D[c] | Immediately wet |
| A | — | — | — | X | N/D | Wettable |
| B | — | X | — | — | <50 | Slight[d] |
| B | — | — | X | — | <50 | Moderate[e] |
| B | X | — | — | — | 62 | Slight[d] |
| B | X | — | — | X | N/D | Immediately wet |
| B | — | — | — | X | N/D | Wettable |

[a]In dynes/cm ($10^{-5}$ newtons/cm).
[b]The sample was not wettable at the higher value, but was wettable at the lower value. Insufficient sample was available to test with Politest surface tension liquids having intermediate values.
[c]Not determined.
[d]Slight, nonuniform wettability.
[e]Moderate, nonuniform wettability.

The use of fibrinogen and surfactant in the same solution (Solutions B or C) did not provide webs with uniform water wettability. ESCA determinations (not shown) indicated the absence of nitrogen on the surfaces of the webs, suggesting that the fibers of the webs were not effectively coated with fibrinogen. Treatment of webs with surfactant after the webs were coated with protein (Solution A followed by Solution D) produced webs having rapid, i.e., immediate, wettability similar to that found after heating or aging protein-coated webs produced from polypropylene containing a surfactant as a melt additive. Thus, water wettability results from a protein-coated surface having present thereon a small quantity of surfactant. Significantly, the coating of either Web A or Web B with fibrinogen, followed by treatment with surfactant, produced webs having better wettability properties (more rapid wetting) than Webs A and B treated with surfactant alone.

As pointed out earlier, the rate of liquid penetration or the distance a fluid moves between fibers per unit time as it penetrates (wets) a porous substrate is directly proportional to the surface tension of the liquid and the cosine of the contact angle of the liquid on the surface of a porous substrate. Because the protein coating significantly raised the surface free energy of the web (to about 58 dynes/cm or about $58 \times 10^{-5}$ newtons/cm), the surface tension of the aqueous liquid needed to be decreased only a modest amount in order to result in wettability. However, the surfactant treatment alone must decrease the surface tension of the water to less than the surface free energy of the polypropylene surface (36 dynes/cm or $36 \times 10^{-5}$ newtons/cm) to be wettable, and therefore there is less penetration power or movement of liquid per unit time than with the webs of the present invention.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A wettable article for exposing to an aqueous liquid having a certain surface tension, said article comprising a hydrophobic surface, the surface having a coating comprising a surface free energy modifier and a surface-active agent so that said article is wettable by said aqueous liquid when exposed thereto, wherein:

said surface free energy modifier has a surface free energy greater than that of said hydrophobic surface but less than the surface tension of said aqueous liquid;

said surface free energy modifier substantially covers said hydrophobic surface; and said surface free energy modifier is present on said surface before said surface-active agent is present in said coating.

2. The wettable article of claim 1, wherein the hydrophobic surface comprises a hydrophobic polymer.

3. The wettable article of claim 2, wherein the hydrophobic polymer is a polyolefin.

4. The wettable article of claim 3, wherein the hydrophobic polymer is polypropylene.

5. The wettable article of claim 1, wherein the surface free energy modifier is a protein.

6. The wettable article of claim 5, in which the protein has a weight-average molecular weight of at least about 10,000 Daltons.

7. The wettable article of claim 6, wherein the protein is selected from the group consisting of fibrinogen, albumin, casein, hemoglobin, and lysozyme.

8. The wettable article of claim 7, wherein the protein is fibrinogen.

9. The wettable article of claim 7, wherein the protein is hemoglobin.

10. The wettable article of claim 1, wherein the surface-active agent is a polyethoxylated alkylphenol.

11. The wettable article of claim 1, wherein the surface-active agent is present in an amount effective to lower the surface tension of said liquid to a value which is greater than the surface free energy of the surface of the article and equal to or less than the surface free energy of the surface free energy modifier.

12. The wettable article of claim 1, wherein the article is selected from the group consisting of a film and fibrous sheet.

13. The wettable article of claim 12, wherein the article is a fibrous sheet.

14. The wettable article of claim 13, wherein the article is a nonwoven web.

15. A disposable absorbent product, a component of which is the wettable article of claim 1.

16. A disposable absorbent diaper, a component of which is the wettable article of claim 1.

17. A disposable absorbent feminine care product, a component of which is the wettable article of claim 1.

18. A disposable absorbent incontinent product, a component of which is the wettable article of claim 1.

19. A wettable article for exposing to an aqueous liquid having a certain surface tension, said article comprising a hydrophobic surface, an internally added surface-active agent that is adapted to migrate to the surface of said article, and a coating comprising a surface free energy modifier so that said article is wettable by said aqueous liquid when exposed thereto, wherein:

said internally added surface-active agent has migrated to said surface of said article after said surface has been coated with said surface free energy modifier;

said surface free energy modifier has a surface free energy greater than that of said hydrophobic surface but less than the surface tension of said aqueous liquid; and said surface free energy modifier substantially covers said hydrophobic surface.

* * * * *